(12) United States Patent
Denner et al.

(10) Patent No.: US 10,590,387 B2
(45) Date of Patent: Mar. 17, 2020

(54) CD133+ CELLS AND METHOD FOR EXPANDING

(71) Applicants: THE BOARD OF REGENTS, THE UNIVERSITY OF TEXAS SYSTEM, Austin, TX (US); Larry Denner, Galveston, TX (US); Randall J. Urban, Galveston, TX (US); Yvonne Bodenburg, Galveston, TX (US)

(72) Inventors: Larry Denner, Galveston, TX (US); Randall J. Urban, Galveston, TX (US); Yvonne Bodenburg, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 172 days.

(21) Appl. No.: 15/567,128

(22) PCT Filed: Apr. 15, 2016

(86) PCT No.: PCT/US2016/027737
§ 371 (c)(1),
(2) Date: Oct. 17, 2017

(87) PCT Pub. No.: WO2016/168586
PCT Pub. Date: Oct. 20, 2016

(65) Prior Publication Data
US 2018/0100140 A1 Apr. 12, 2018

Related U.S. Application Data

(60) Provisional application No. 62/148,963, filed on Apr. 17, 2015.

(51) Int. Cl.
*C12N 5/0775* (2010.01)
*C07K 16/28* (2006.01)

(52) U.S. Cl.
CPC ........ *C12N 5/0665* (2013.01); *C07K 16/2896* (2013.01)

(58) Field of Classification Search
None
See application file for complete search history.

(56) References Cited

U.S. PATENT DOCUMENTS 8,080,417 B2  12/2011  Peled et al.
2012/0177614 A1*  7/2012  Kido ................... C12N 5/0622
424/93.7

FOREIGN PATENT DOCUMENTS

WO  WO 2010/138873 A1  12/2010

OTHER PUBLICATIONS

Alakel et al., "CD133+ purified hematopoietic stem cells in co-culture with mesenchymal stromal cells—the cell to cell contact matters," Poster Session, *Blood (ASH Annual Meeting Abstracts)*, 2007; 110:Abstract 1421.
Alakel, et al., "Direct contact with mesenchymal stromal cells affects migratory behavior and gene expression profile of CD133+ hematopoietic stem cells during ex vivo expansion," *Exp Hematol*, 2009; 37(4):504-513.
Bernardi et al., "The isolation of stem cells from human deciduous teeth pulp is related to the physiological process of resorption," *J Endod*, 2011; 37(7):973-979.
DeLima et al., "Cord-blood engraftment with ex vivo mesenchymal-cell coculture," *N Engl J Med*, 2012; 367(24):2305-2315.
Denner et al., "Directed engineering of umbilical cord blood stem cells to produce C-peptide and insulin," *Cell Prolif*, 2007; 40(3):367-380.
Fasouliotis et al., "Human umbilical cord blood banking and transplantation: a state of the art," *Eur J Obstet Gynecol Reprod Biol*, 2000; 90(1):13-25.
Gay et al., "CD133 expression correlates with membrane beta-catenin and e-cadherin loss from human hair follicle placodes during morphogenesis," *J Invest Dermatol*, 2015; 135(1):45-55.
Gu et al., "Isolation and differentiation of neural stem/progenitor cells from fetal rat dorsal root ganglia," *Sci China Life Sci*, 2010; 53(9):1057-1064.
Hager et al., "Three specific antigens to isolate endothelial progenitor cells from human liposuction material," *Cytotherapy*, 2013; 15(11):1426-1435.
Howe, "Signaling pathways regulating self-renewal, differentiation, and multipotency of CD133+ umbilical cord blood stem cells," Doctoral Dissertation, Sep. 2008, The University of Texas Medical Branch, 100 pages.
Howe et al., "Oct-4A isoform is expressed in human cord blood-derived CD133 stem cells and differentiated progeny," *Cell Prolif*, 2009; 42(3):265-275.
Inage et al., "Critical roles for PU.1, GATA1, and GATA2 in the expression of human FcεRI on mast cells: PU.1 and GATA1 transactivate FCER1A, and GATA2 transactivates FCER1A and MS4A2," *J Immunol*, 2014; 192(8):3936-3946.
International Preliminary Report on Patentabiliby, PCT/US2016/027737, dated Oct. 17, 2017; 10 pages.
International Search Report and Written Opinion, PCT/US2016/027737, dated Aug. 8, 2016; 13 pages.
Kelly et al, "Ex vivo expansion of cord blood," *Bone Marrow Transplant*, 2009; 44(10):673-681.
Maslova et al., "Enrichment of umbilical cord blood mononuclears with hemopoietic precursors in co-culture with mesenchymal stromal cells from human adipose tissue," *Cell Technologies in Biology and Medicine*, 2014; 4:584-589.
Novershtern et al., "Densely interconnected transcriptional circuits control cell states in human hematopoiesis," *Cell*, 2011; 144:296-309.

(Continued)

*Primary Examiner* — Daniel C Gamett
(74) *Attorney, Agent, or Firm* — Mueting, Raasch & Gebhardt, P.A.

(57) ABSTRACT

Provided herein are isolated CD133+ cells, such as human CD133+ cells, that have been expanded in culture and populations of isolated CD133+ cells that have been expanded in culture. The cells express transcription factors, growth factors, or a combination thereof, at altered levels compared to a naturally occurring CD133+ cell. Also provided are methods, including methods for expanding CD133+ cells and methods for using CD133+ cells.

24 Claims, 3 Drawing Sheets

(56) References Cited

OTHER PUBLICATIONS

Pagliuca et al., "Generation of functional human pancreatic β cells in vitro," *Cell*, 2014; 159(2):428-439.
Pezzolla et al., "Resveratrol ameliorates the maturation process of β-cell-like cells obtained from an optimized differentiation protocol of human embryonic stem cells," *PLoS One*, 2015; 10(3):e0119904; 21 pages.
Robinson et al., "Superior ex vivo cord blood expansion following co-culture with bone marrow-derived mesenchymal stem cells," *Bone Marrow Transplant*, 2006; 37(4):359-366.
Shmelkov et al., "CD133 expression is not restricted to stem cells, and both CD133+ and CD133− metastatic colon cancer cells initiate tumors," J Clinical Investigation, 2008; 118(6):2111-2120.
Vaiselbuh et al., "Short-term ex vivo expansion of CD133+ cells by co-culture with mesenchymal stem cells: Role of SDF-1/CXCL12," Abstract 3471, 50$^{th}$ ASH Annual Meeting and Exposition, San Francisco, CA, Dec. 6-9, 2008; 1 page.
Wang et al., "CD133/CD140a-based isolation of distinct human multipotent neural progenitor cells and oligodendrocyte progenitor cells," *Stem Cells and Development*, 2013; 22(15):2121-2131.
Walasek et al., "Hematopoietic stem cell expansion: challenges and opportunities," *Ann NY Acad Sci*, 2012; 1266:138-150.
Yi et al., "Foxa2 acts as a co-activator potentiating expression of the Nurr1-induced DA phenotype via epigenetic regulation," *Development*, 2014; 141(4):761-772.

\* cited by examiner

CD133+ CELLS AND METHOD FOR EXPANDING

CROSS-REFERENCE TO RELATED APPLICATIONS

This application is the § 371 U.S. National Stage of International Application No. PCT/US2016/027737, filed Apr. 15, 2016, which claims the benefit of U.S. Provisional Application Ser. No. 62/148,963, filed Apr. 17, 2015, both of which are incorporated by reference herein.

SUMMARY OF THE APPLICATION

Provided herein are isolated CD133+ cells, such as human CD133+ cells. The isolated human CD133+ cells express at least one mRNA selected from FOXA2, HOXA1, MKI67, and PCNA at a higher level than a naturally occurring human CD133+ cell, expressing at least one mRNA selected from TCF7, KLF1, BMP3, GATA1, GATA3, IL18R1, and GDF10 at a lower level than a naturally occurring human CD133+ cell, or a combination thereof. In one embodiment, 1, 2, 3, or all 4 FOXA2, HOXA1, MKI67, and PCNA mRNAs are expressed at a higher level in the isolated CD133+ cell than in the naturally occurring human CD133+ cell. In one embodiment, 1, 2, 3, 4, 5, 6, or all 7 TCF7, KLF1, BMP3, GATA1, GATA3, IL18R1, and GDF10 mRNAs are expressed at a lower level in the isolated CD133+ cell than in the naturally occurring human CD133+ cell. In one embodiment, a combination of one or more mRNAs selected from FOXA2, HOXA1, MKI67, and PCNA are expressed in the isolated CD133+ cell at a higher level than a naturally occurring human CD133+ cell and a combination of one or more mRNAs selected from TCF7, KLF1, BMP3, GATA1, GATA3, IL18R1, and GDF10 are expressed in the isolated CD133+ cell at a lower level than a naturally occurring human CD133+ cell. The CD133+ cells may be modified or non-modified.

In one embodiment, the difference in expression of an mRNA in the isolated CD133+ cell compared to the mRNA in the naturally occurring human CD133+ cell is statistically significant. In one embodiment, the isolated CD133+ cell grows at a rate that is greater than the naturally occurring human CD133+ cell. In one embodiment, the naturally occurring human CD133+ cell is from cord blood.

Also provided is a population of isolated human CD133+ cells. In one embodiment, members of the population express at least one mRNA selected from FOXA2, HOXA1, MKI67, and PCNA at a higher level than a naturally occurring human CD133+ cell. In one embodiment, members of the population express at least one mRNA selected from TCF7, KLF1, BMP3, GATA1, GATA3, IL18R1, and GDF10 at a lower level than a naturally occurring human CD133+ cell. In one embodiment, 1, 2, 3, or all 4 FOXA2, HOXA1, MKI67, and PCNA mRNAs are expressed at a higher level in members of the population than in a naturally occurring human CD133+ cell. In one embodiment, 1, 2, 3, 4, 5, 6, or all 7 TCF7, KLF1, BMP3, GATA1, GATA3, IL18R1, and GDF10 mRNAs are expressed at a lower level in the members of the population than in a naturally occurring human CD133+ cell. In one embodiment, a combination of one or more mRNAs selected from FOXA2, HOXA1, MKI67, and PCNA are expressed in members of the population at a higher level than in a naturally occurring human CD133+ cell and a combination of one or more mRNAs selected from TCF7, KLF1, BMP3, GATA1, GATA3, IL18R1, and GDF10 are expressed in members of the population at a lower level than a naturally occurring human CD133+ cell.

Also provided herein are methods. In one embodiment, a method is for producing an expanded population of CD133+ cells. In one embodiment, the method includes providing a sample that includes isolated human CD133+ cells, and incubating the CD133+ cells for at least 1 day in a first culture under conditions suitable for division of the CD133+ cells. The CD133+ cells present in the first culture are reisolated to result in first reisolated CD133+ cells. These first reisolated cells are incubated for at least 1 day in a second culture under conditions suitable for division of the CD133+ cells, and the CD133+ cells present in the culture are reisolated a second time. In one embodiment, this incubating and the second reisolating can be repeated until the CD133+ cells are cultured at least 21 days after the first reisolating. In one embodiment, this incubating and the second reisolating can be repeated until at least 15% of the cells after the at least 1 day incubation in the second culture are CD133+.

In one embodiment, the incubating in the first culture can be for at least 4 days, and in one embodiment, for no greater than 21 days. In one embodiment, the incubating in the second culture is for at least 7 days. In one embodiment, the isolating and reisolating includes use of an antibody that specifically binds a CD133 epitope. Such an antibody can be attached to a matrix, including a bead. In one embodiment, the isolating and reisolating includes flow cytometry. In one embodiment, the reisolating includes removal of substantially all CD133− cells.

In one embodiment, the sample is obtainable by isolating human CD133+ cells away from human CD133− cells. The isolating can include processing a biological sample to increase the amount of CD133+ cells relative to the amount of CD133− cells by at least 2-fold. In one embodiment, the sample includes cells originating from banked umbilical cord blood.

The sample can be fresh or frozen. In one embodiment, the sample includes CD133+ cells originating from connective tissue, nervous tissue, epithelial tissue, mineralized tissue, a hematopoietic source, or an organ. The connective tissue can include adipose tissue, intestine, or hair follicle. The nervous tissue can include central or peripheral nervous system compartments including brain, sciatic nerve, ganglia, retina, or cardiac outflow tract. The ganglia can include spinal ganglia or sympathetic ganglia. The epithelial tissue can include olfactory epithelium, skin, ovarian epithelium, blood vessel, or intestine. The blood vessel can include endothelium. The mineralized tissue can include tendon, cartilage, or tooth. The hematopoietic source can include bone marrow, peripheral blood, blood vessel, lymph, umbilical cord blood, or Wharton's jelly. The organ can include brain, skin, heart, liver, intestine, placenta, lung, testis, breast, or placenta.

In one embodiment, a method includes providing human CD133+ cells that have been cultured ex vivo for at least 21 days, culturing the human CD133+ cells for at least 1 day and no greater than 20 days under conditions suitable for division of the CD133+ cells, isolating the CD133+ cells present in the culture wherein at least 15% of the cells after the culturing are CD133+. The method can further include expanding the number of CD133+ cells by repeating the culturing and isolating steps at least once.

DETAILED DESCRIPTION OF ILLUSTRATIVE EMBODIMENTS

Figure 1:
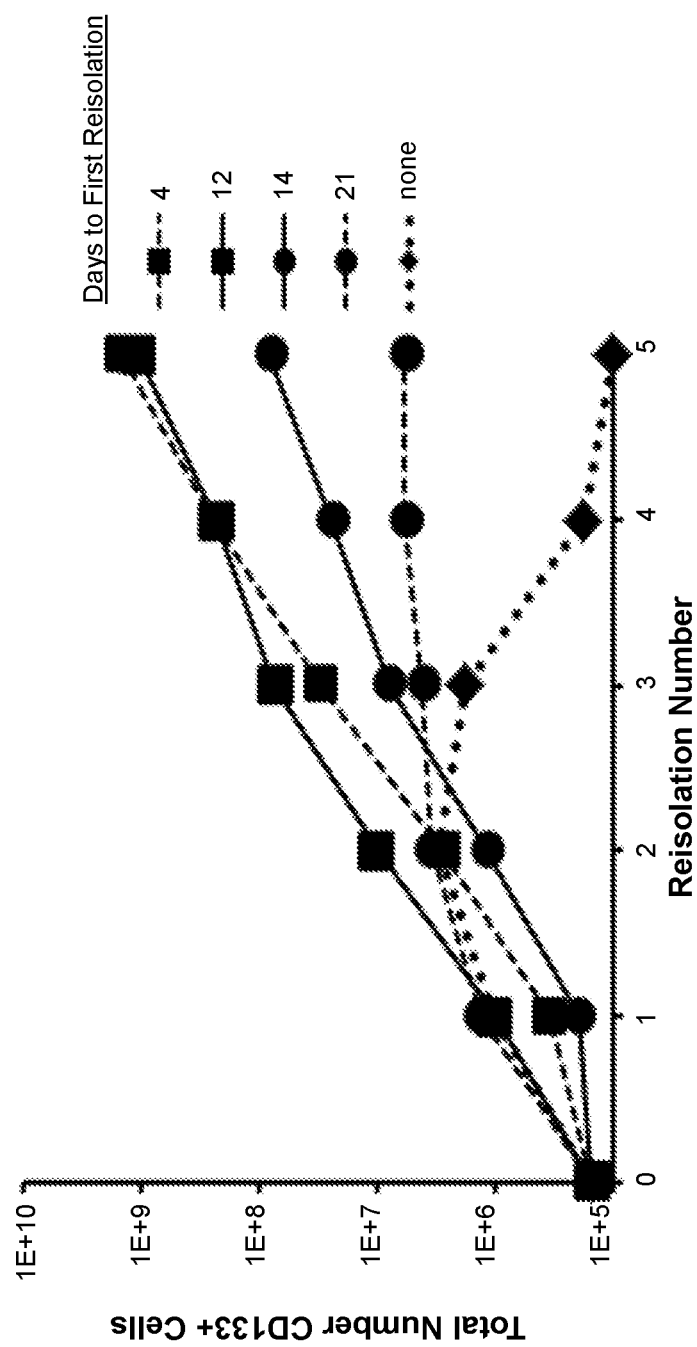
FIG. 1. Effects of Initial Culture Duration on Total Number of CD133+ Cells.

Provided herein are methods for producing a population of CD133+ cells. In one embodiment, the methods include expansion of an initial or starter population of CD133+ cells in the presence of a feeder layer and increasing the number of CD133+ cells to result in a renewable population of CD133+ cells. The renewable population of CD133+ cells can be used in a variety of applications, including transplantation. In contrast to other methods for obtaining expanded populations of CD133+ cells, the methods described herein provide long term expansion of CD133+ cells in sufficient numbers for use in therapies such as transplantation. The CD133+ cells include hematopoietic stem cells and progenitor cells. The methods described herein also select for CD133+ cells that express a greater amount of more primitive markers than are expressed by CD133+ cells in a body, such as a human body.

In one embodiment, the method includes isolating CD133+ cells from a mixture of CD133+ and CD133− cells that are present in a sample. As used herein, "isolating," "isolated," "reisolating," and "reisolated," means that the amount of CD133+ cells relative to the amount of CD133− cells has been increased at least 2-fold, at least 5-fold, at least 10-fold, or at least 15-fold compared to the amount of CD133+ cells relative to the amount of CD133− cells before the isolation or reisolation. As used herein, isolation of CD133+ cells does not imply that all CD133− cells have been removed.

In one embodiment, the sample may be a biological sample obtainable from any source that contains CD133+ cells. Examples of sources of CD133+ cells include many organs and tissues, such as, but not limited to, connective tissue (e.g., adipose tissue, intestine, hair follicle); muscle tissue (e.g., skeletal muscle, heart); nervous tissue (e.g., sciatic nerve, ganglia [such as spinal ganglia or sympathetic ganglia], retina, cardiac outflow tract); epithelial tissue, (e.g., olfactory epithelium, skin, ovarian epithelium, olfactory epithelium, blood vessels [including endothelium], intestine); mineralized tissue, (e.g., tendon, cartilage, tooth); hematopoietic (blood) sources (e.g., bone marrow, peripheral blood, blood vessels [including endothelium], lymph, umbilical cord blood, Wharton's jelly); and organs, (e.g., brain, skin, heart, liver, intestine, placenta, lung, testis, breast, placenta). Hematopoietic stem cells and progenitor cells, including CD133+ cells, are thought to reside in a specific area of each tissue (called a "stem cell niche") in all parts of the body. In one embodiment, a CD133+ cell may be a hematopoietic stem cell or a progenitor cell, e.g., a cell obtained from a blood source such as umbilical cord blood. The animal used as a source of the biological sample can be a mammal, including but not limited to, a human, a bovine, an equine, a canine, a feline, a porcine, an ovine, or a murine (a mouse or a rat).

In one embodiment, the biological sample used in the method has been processed to remove many of the CD133− cells, e.g., red blood cells and granulocytes, to result in isolated CD133+ cells. The biological sample may be fresh or one that has been stored as a frozen sample. An example of a frozen sample is banked human umbilical cord blood cells (Fasouliotis et al. Eur J Obst Gyn Repro Biol., 2000, 90(1):13-25).

In one embodiment, the method also includes obtaining the biological sample from a subject, and/or processing the biological sample to remove many of the CD133− cells to result in isolated CD133+ cells. A biological sample typically includes a large variety of cells, and methods for removing many of the CD133− cells, e.g., red blood cells and granulocytes, are known to the skilled person. While many methods for isolating CD133+ cells can be used, this typically includes applying a biological sample onto Ficoll-Paque and collecting, following density-gradient centrifugation, the "buffy coat" interface layer present between the blood serum and the red blood cells, a layer that includes the white blood cells present in the blood sample. In one embodiment, the processed sample may be used immediately in the following culturing step, or the processed sample may be frozen and stored before use in the following culturing step.

Methods for isolating CD133+ cells from CD133− cells are known in the art and are routine. At the present time, methods often use an antibody that recognizes and binds the CD133 antigen on the surface of CD133+ cells. The use of antibody permits further separation of cells after a centrifugation (e.g., use of a Ficoll-Paque layer). The separation is routine and immuno-separation can be performed using techniques such as immunomagnetic separation or fluorescence activated flow cytometry. Such methods may include the use of a matrix to which an antibody is bound, such as a bead. Antibodies that recognize and bind CD133 are readily available commercially. During an isolation and/or reisolation the fractions that do not include high levels of CD133+ cells can be discarded or reserved. CD133+ cells can also be isolated by many other methods such as those based on gene and/or protein expression, electrical properties such as impedance, or other properties such as calcium abundance, apoptotic profiles, or mitochondrial membrane potential.

The isolated CD133+ cells are typically incubated as a suspension culture under conditions suitable for division of the CD133+ cells. The methods used for the culturing of the cells are known in the art and routine (see, for instance Walasek et al., Ann NY Acad Sci 2012, 1266:138). The methods include the use of standard media, and the methods disclosed herein are not limited by the medium used, or by any supplements used in the medium. Examples of media that may be used to culture the cells may include, but are not limited to, Iscove's-modified Dulbecco's medium. Standard supplements typically used in cell culture to promote growth and division of cells may be included, such as serum, fetal bovine serum, other proteins and their replacements, and cytokines and growth factors. Throughout the method, routine tissue culture techniques are used, including regular feeding of the cultures.

The culturing of the isolated CD133+ cells may include the use of a feeder cell layer. Typically, the feeder cell layer is mesenchymal stem cells (MSCs) derived from various sources including umbilical cord matrix (Wharton's jelly), such as human MSCs. The use of MSCs for co-culture with CD133+ cells is known and routine (Alakel et al., Exp Hematol 2009, 37:504; Robinson et al., Bone Mar Transpl 2006, 37:359), and MSCs are commercially available. The MSCs may be actively growing in co-culture with the CD133+ cells, or not growing due to growth-inhibiting processes such as irradiation or chemical treatment. In one embodiment, the CD133+ cells can be placed in medium so they may contact the feeder cells, and in another embodiment the CD133+ cells can be placed in medium so they cannot contact the feeder cells (e.g., a permeable membrane can be placed between the CD133+ cells and the feeder cells such as found in a Boyden Chamber).

Incubating the culture after this first isolation is for at least one day and no greater than 21 days. Thus, the incubating immediately after isolation may be for 1, 2, 3, 4, 5, 6, 7, 8, 9, 10, 11, 12, 13, 14, 15, 16, 17, 18, 19, 20, or 21 days. In one embodiment, the incubating is no greater than 20 days, or no greater than 21 days. In one embodiment, for convenience the incubating is 7 days, and in another embodiment the incubating is for 14 days. During this incubation the CD133+ cells undergo asymmetric division, where each division of a CD133+ cell typically results in a CD133+ daughter cell and a CD133− daughter cell. After the culturing, the cells present in the culture include CD133+ cells, CD133− daughter cells, and cells of the feeder layer. In one embodiment, after the incubating the CD133+ cells may be used immediately in the following reisolation step, or the CD133+ cells may be frozen and stored before use in the following reisolation step.

Without intending to be limiting, during the culturing the CD133+ cells divide to give rise to a CD133+ cell and a CD133− daughter cell. After the culturing, CD133+ cells typically in suspension (not adherent to a surface) are reisolated, and the reisolated CD133+ cells are incubated again under conditions suitable for division of the CD133+ cells. The length of the incubation after reisolation is not intended to be limiting. The incubating is for at least one day, such as at least 1, at least 2, at least 3, at least 4, at least 5, at least 6, at least 7, at least 8, at least 9, at least 10, at least 11, at least 12, at least 13, at least 14 days, or more. In one embodiment, for convenience the incubating is 7 days, and in another embodiment the incubating is for 14 days. The length of the incubation after reisolation is not intended to be limiting. After the incubation the cells present in the culture include CD133+ cells, CD133− daughter cells, and cells of the feeder layer. This process of culturing reisolated CD133+ cells followed by reisolation of CD133+ cells from the culture is repeated for sustained propagation and expansion of CD133+ cells.

The reisolation and culturing process (e.g., reisolation of CD133+ cells followed by culturing the reisolated CD133+ cells) eventually results in a population that reaches a sustained phase of continuous production of CD133+ cells. The population includes CD133+ hematopoietic stem cells and CD133+ progenitor cells. During the sustained phase, the reisolated cells continue to produce a relatively fixed proportion of CD133+ cells compared to CD133− daughter cells. In one embodiment, the fixed proportion is at least 15%, or at least 20% CD133+ cells to no greater than 30% or no greater than 50% CD133+ cells. In one embodiment, the amount of time required to achieve the sustained phase after the first reisolation is at least 2 weeks to no greater than 4 weeks, such as 3 weeks.

The reisolation and culturing process (e.g., reisolation of CD133+ cells followed by culturing the reisolated CD133+ cells) can be repeated as needed to obtain a number of cells deemed useful in practicing methods using CD133+ cells, for instance, at least 5, at least 10, at least 40, at least 60, at least 80 times, or as required for subsequent use. There is no identified upper limit to the number of times the reisolation and culturing process can occur; however, in some embodiments the reisolation and culturing process occurs no greater than 100, no greater than 500, or no greater than 1000 times. In one trial, a 300,000,000-fold expansion of CD133+ cells has been observed when the step of reisolating and culturing was repeated 10 times. Thus, the expansion of the cells may be at least 100,000-fold, at least 1,000,000-fold, at least 300,000,000-fold, at least 500,000,000-fold, or greater, or as required for subsequent use. Because this is a renewable source with a scalable method for expansion, there is no identified upper limit to the expansion that can occur; however, in some embodiments such as islet transplantation for type 1 diabetes 1,000,000,000 cells is useful.

The CD133+ cells may be modified. Modifications include chemical or genetic manipulation such as transfection with DNA or RNA (e.g., a transgene, a microRNA, an siRNA, and the like). Modification of CD133+ cells may take place during any point during the method.

In another embodiment, the CD133+ cells may be non-modified, e.g., the cells used in the method are free of any artificial modification such as genetic manipulation (e.g., no transfection with DNA or RNA).

Provided herein is a method for passaging the CD133+ cells to maintain the sustained phase and expand the number of CD133+ cells. The method includes providing CD133+ cells that have been cultured ex vivo for at least one day and no greater than 21 days would work to a limited extent, for instance, for 1, 2, 3, 4, 5, 6, 7, 8, 9, 10, 11, 12, 13, 14, 15, 16, 17, 18, 19, 20, or 21 days, culturing the CD133+ cells for at least 1 day under conditions suitable for division of the CD133+ cells, and isolating the CD133+ cells present in the culture. In one embodiment, the CD133+ cells continue to produce a fixed proportion of CD133+ cells compared to CD133− daughter cells, where the fixed proportion is at least 15%, or at least 20% CD133+ cells to no greater than 30% or no greater than 50% CD133+ cells. The method may further include continuing to expand the number of CD133+ cells by repeating the culturing and isolating steps.

Also provided herein are isolated CD133+ cells. Optionally, the CD133+ cells are purified to result in a population that typically is >90% CD133+ cells. The results of transcriptional expression profiling show that the CD133+ cells described herein show differential expression of many transcription factors and growth factors. Thus, the CD133+ cells described herein are not phenotypically identical to a population of CD133+ cells naturally present in a body, such as a human body. In one embodiment, an isolated CD133+ cell is a hematopoietic stem cell or a progenitor cell. The cell culture results in CD133+ cells expressing more primitive markers than are expressed by the population of CD133+ cells in a body. This expression of more primitive markers is expected to result in CD133+ cells having a more multipotent, in one embodiment pluripotent, nature than the population of CD133+ cells naturally present in a body, such as a human body.

As described in Example 2, mRNAs encoding FOXA2, HOXA1, MKI67, and PCNA are increased in CD133+ cells expanded for four weeks in culture compared to CD133+ cells freshly isolated from cord blood. mRNAs encoding FLT3, RUNX2, TCF4, POU5F1, SOX4, TCF7, KLF1, BMP3, GATA1, GATA3, IL18R1, and GDF10 are decreased in CD133+ cells expanded for four weeks in culture compared to CD133+ cells freshly isolated from cord blood. Isolated CD133+ cells described herein can have increased expression of mRNAs encoding FOXA2, HOXA1, MKI67, and PCNA in any combination, e.g., 1, 2, or 3 of the mRNAs in any combination, or all 4 of the mRNAs. Isolated CD133+ cell described herein can have decreased expression of mRNAs encoding FLT3, RUNX2, TCF4, POU5F1, SOX4, TCF7, KLF1, BMP3, GATA1, GATA3, IL18R1, and GDF10 in any combination, e.g., 1, 2, 3, 4, 5, 6, 7, 8, 9, 10, or 11 of the mRNAs in any combination, or all 12 of the mRNAs. Likewise, isolated CD133+ cells described herein can have any combination of mRNAs having increased expression and mRNAs having decreased expression.

The change in expression of these transcription factors and growth factors (increased or decreased) is statistically significant. In one embodiment, the increase of expression of an mRNA encoding FOXA2 can be 9 log FC, the increase of expression of an mRNA encoding HOXA1 can be 2.8 log FC, the increase of expression of an mRNA encoding MKI67 can be 2.8 log FC, and the increase of expression of an mRNA encoding PCNA can be 2 log FC. In one embodiment, the decrease of expression of an mRNA encoding TCF7 can be −2.3 log FC, the decrease of expression of an mRNA encoding KLF1 can be −2.4 log FC, the decrease of expression of an mRNA encoding BMP3 can be −3.4 log FC, the decrease of expression of an mRNA encoding GATA1 can be −5 log FC, the decrease of expression of an mRNA encoding GATA3 can be −7.8 log FC, the decrease of expression of an mRNA encoding IL18R1 can be −8 log FC, and the decrease of expression of an mRNA encoding GDF10 can be −8 log FC.

Further provided herein is a population of isolated CD133+ cells. In one embodiment, a subset of CD133+ cells also express CD45. That subset can be at least 80%, at least 90%, or each member of the population of isolated CD133+ cells. In one embodiment, a subset of CD133+ cells also express CD34. That subset can be at least 40% or at least 50% of the population of isolated CD133+ cells expressing both CD133 and CD45. In one embodiment, the population of CD133+ cells includes CD133+ cells that are hematopoietic stem cells or progenitor cells.

Also provided herein are methods for using the expanded cells. Uses of CD133+ cells include cell transplantations, cellular gene therapy, adoptive immunotherapy, treatments of diseases, for example, by implantation of cells for in vivo tissue and organ regeneration and ex vivo tissue engineering for tissue and organ regeneration.

In one embodiment, a method includes treating a disease and/or a condition in a subject. The subject is a mammal, including, but not limited to, a human, a bovine, an equine, a canine, a feline, a porcine, an ovine, or a murine (a mouse or a rat). As used herein, the term "disease" refers to any deviation from or interruption of the normal structure or function of a part, organ, or system, or combination thereof, of a subject that is manifested by a characteristic symptom or set of symptoms. A "condition" is one or more symptoms and/or signs resulting from a disease. The use of cells as a therapeutic is expected to be useful in treating many diseases and conditions. Diseases and conditions include, for example, hematopoietic malignancies, treatments that include myeloablation, and autologous or allogeneic cell therapy promoting the regeneration of any tissue or organ. Specific diseases and conditions include, but are not limited to, diabetes, bone marrow transplant, rheumatoid arthritis, Parkinson's disease, Alzheimer's disease, osteoarthritis, stroke and traumatic brain injury repair, spinal cord injury repair, heart infarction or failure, renal failure, cancer, hearing loss, vision loss, amyotrophic lateral sclerosis, Crohn's disease, and wound healing. Typically, whether a subject has a disease and/or a condition, and whether a subject is responding to treatment, is determined by evaluation of symptoms associated with the disease. As used herein, the term "symptom" refers to subjective evidence of disease or condition experienced by the patient and caused by a disease. As used herein, the term "clinical sign" or, simply, "sign" refers to objective evidence of disease or condition. Symptoms and/or clinical signs associated with diseases and conditions referred to herein and the evaluations of such symptoms are routine and known in the art.

Treating a subject, such as a subject having diabetes, can be prophylactic or, alternatively, can be initiated after the need for treatment arises. Treatment that is prophylactic, for instance, initiated before a subject manifests symptoms of a condition, is referred to herein as treatment of a subject that is "at risk" of developing the condition. Typically, a subject "at risk" of developing a condition is a subject likely to have a genetic predisposition to having the disease or condition. Accordingly, administration of CD133+ cells can be performed before, during, or after the occurrence of a disease or condition. Treatment initiated after the development of a condition may result in decreasing the severity of the symptoms of one of the conditions, or completely removing the symptoms.

Treating a disease and or condition in a subject includes administering CD133+ cells to the subject. The cells can be directly administered into the bloodstream, encapsulated in a three dimensional natural or artificial structure, or placed in a particular restricted location including, but not limited to, the renal capsule. The CD133+ cells may be manipulated in culture by directed differentiation to produce cells with disease-specific characteristics. For example, CD133+ cells can be differentiated to produce insulin (Denner et al. 2007, Cell Prolif. 40:367) or using methods described in the literature for directed differentiation of human embryonic or induced pluripotent stem cells (Pagliuca et al. 2014, Cell, 159:428; Pezzolla et al. 2015, PLoS One, 10:e0119904.).

Also provided is a method for preserving the CD133+ cells. In one embodiment, the method includes the use of a cryopreservative, such as DMSO. Methods for preparing cells for freezing are known and routine.

As used herein, a "cell" refers to a cell that is relatively undifferentiated and can differentiate into a specialized cell. A cell may refer to a stem cell capable of self-renewal, e.g., able to undergo multiple cycles of cell division and continue to produce undifferentiated cells. A stem cell may be multipotent or pluripotent. Multipotent refers to a stem cell that has the ability to differentiate into many, but not all, cell types. Pluripotent refers to a stem cell that has the ability to differentiate into any of the three germ layers of endoderm, mesoderm, or ectoderm.

As used herein, "ex vivo" refers to a cell that has been removed from the body of an animal. "Ex vivo culture" refers to propagation of an ex vivo cell outside the body of an animal, such as in a container used for tissue culture.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

In several places throughout the application, guidance is provided through lists of examples, which examples can be used in various combinations. In each instance, the recited list serves only as a representative group and should not be interpreted as an exclusive list.

The present invention is illustrated by the following examples. It is to be understood that the particular examples, materials, amounts, and procedures are to be interpreted broadly in accordance with the scope and spirit of the invention as set forth herein.

Example 1

It was shown several years ago that human umbilical cord blood (UCB) CD133+ cells could be grown and expanded in culture for a limited time. These cells typically undergo asymmetric division producing CD133+ and differentiated CD133− daughter dells. While the CD133+ cells continue to expand, the ability to produce CD133+ daughter cells diminishes over the course of several weeks, ultimately producing no new CD133+ cells. This limited number of CD133+ cells has presented an insurmountable barrier to their utility in transplantation settings. The purpose of the current studies was to overcome this limitation to grow high numbers of UCB CD133+ cells. Reported here is the observation that co-culturing freshly isolated human UCB CD133+ cells with human meschenchymal stem cells (MSCs) for a limited period of time followed by weekly removal of the CD133− daughter cells results in the selection of a population of CD133+ cells that will produce a sustained level of CD133+ daughter cells.

Materials and Methods

Isolation of Adult Human Umbilical Cord Blood Cells

Umbilical cord blood (UBC) units were collected from donors and diluted upon collection with phosphate buffered saline (Sigma-Aldrich, St Louis, Mo., U.S.A.) supplemented with 0.6% acid citrate dextrose formula-A acid anti-coagulant (Sigma-Aldrich) and bovine serum albumin (0.5% fraction V, Sigma-Aldrich) at pH 7.4 (ACD-A). Four volumes of diluted UCB units were overlaid onto one volume of research grade Ficoll-Paque solution (d: 1.077 g/cm$^3$, Amersham Biosciences, Uppsala, Sweden) following the manufacturer's instructions. Following centrifugation at 400 g for 30 minutes at room temperature, the mononuclear layer was removed, washed twice in ACD-A buffer, and used for further purification. CD133+ cells were isolated as previously described (Howe M et al. 2009 Cell Prolif 42:265; Denner et al. 2007 Cell Prolif 40:367) by positive selection with colloidal super-paramagnetic MACS MicroBeads conjugated to monoclonal mouse anti-human CD133 antibodies (Miltenyi Biotec Inc., Germany).

Flow Cytometry

Approximately 100,000 cells were incubated at 4° C. for 30 minutes with anti-human CD133 antibody conjugated to phycoerythrin (PE) (MACS, Germany). Negative controls were incubated with mouse IgG isotype control PE (StemCell Technologies). Cells were centrifuged, washed, fixed with 0.5% paraformaldehyde, and kept refrigerated until flow cytometry analysis within one week using a BD FACSCanto (BD Biosciences, USA) with excitation/emission for FITC at 488/530.

Human Mesenchymal Stem Cells

Human mesenchymal stem cells (MSCs) were purchased from PromoCell and grown in MSC Growth medium with Supplement Mix (PromoCell) and 1× Penicillin Streptomycin. MSCs were expanded in culture and passaged using trypsin in the Detach Kit (PromoCell) specific for MSCs. Cells were frozen at low passage number in Freezing Media Cryo-SFM (PromoCell). The day before umbilical cord blood CD133+ cells were isolated, MSCs growing in MSC Growth medium were trypsinized and counted. MSCs were plated at the following densities: 100,000 cells in 60 mm tissue culture plate and 200,000 cells in 100 mm tissue culture plates.

Cytokine-Induced Expansion of UCB Cells

UCB cells ($10^4$ cells/ml) were cultured in tissue culture microflasks (Nunc, Rochester, N.Y.) at 37° C., 5% $CO_2$ humidified atmosphere in Iscove's-modified Dulbecco's medium (IMDM, Invitrogen, Carlsbad, Calif.) supplemented with 10% fetal bovine serum (Es-Cult™-Tested FBS, StemCell Technologies Inc.) in the presence of the human recombinant cytokines (Pepro Tech, Inc., NJ) thrombopoietin (10 ng/ml) and flt3-ligand (50 ng/ml). Medium and cytokines were replenished every 3-4 days with reseeding of cells onto fresh MSCs.

Results

Figure 2:
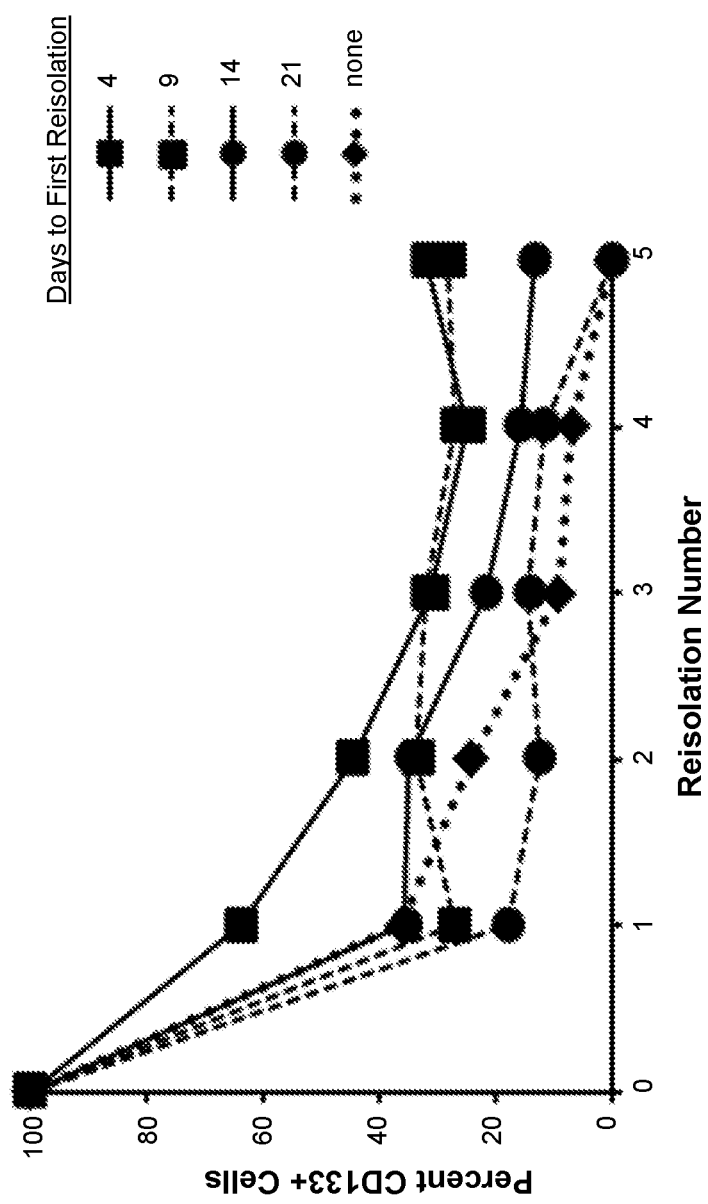
FIG. 2. Effects of Initial Culture Duration on Percentage of CD133+ Cells.
Figure 3:
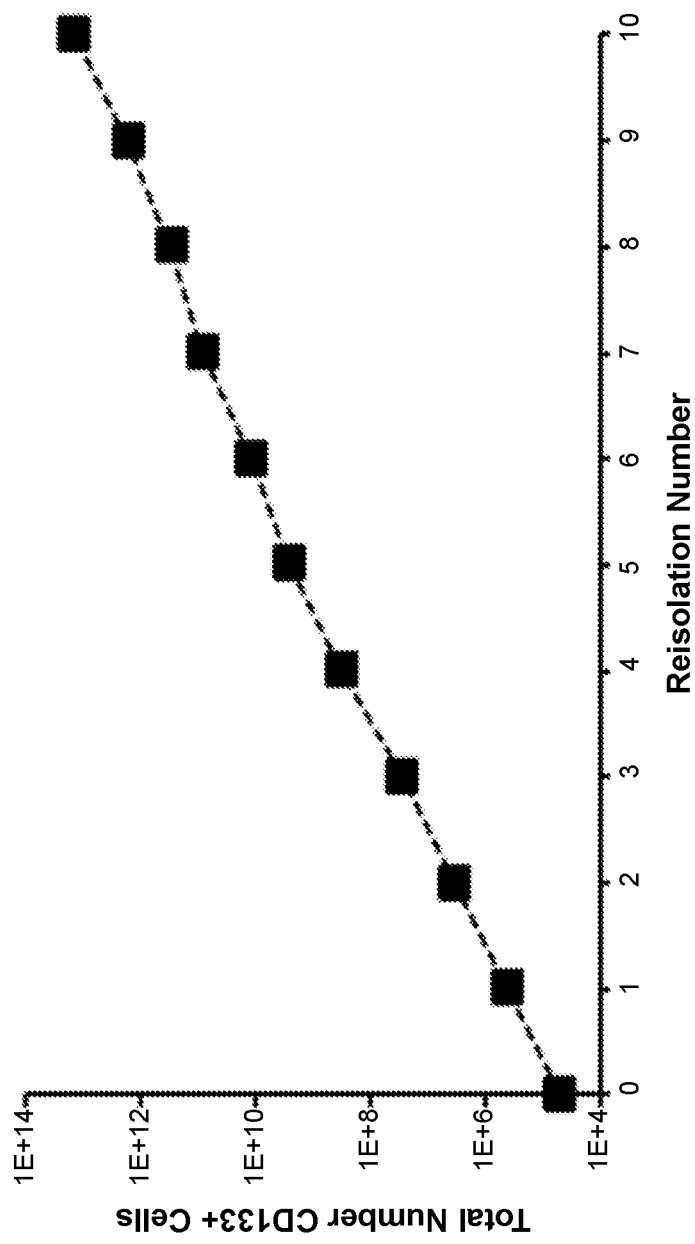
FIG. 3. Expansion of CD133+ "Sustained" Cells.

Freshly isolated human UCB CD133+ cells were co-cultured with adherent human MSCs for 4-21 days. CD133− cells were then removed by immunoaffinity bead isolation of CD133+ cells. The reisolated CD133+ cells were replated onto fresh MSCs for continued culture. This process of CD133+ reisolation and replating onto fresh MSCs was subsequently repeated at weekly intervals. Using cell counting and flow cytometry, the number and purity of CD133+ cells were assessed at each time point. We found that 4-14 days of initial culture followed by weekly reisolation resulted in continued expansion of CD133+ cells (FIG. 1, where zero on the x-axis refers to time cells placed in culture after 4-21 days of initial culture). While a similar response was found for initial culture periods of less than 4 days, overall growth was relatively low making shorter initial durations less productive. After 2-3 weekly reisolations the cells reached a sustained plateau phenotype that continued to produce a fixed proportion (~20-30%) of CD133+ cells (FIG. 2, where zero on the x-axis refers to time cells placed in culture after 4, 9, 14, or 21 days of initial culture, or no initial culture). This sustained cell phenotype has been identified in each of the 23 tested different isolations from independent collections of cord blood. We have followed one UCB isolation for 10 reisolations wherein 5E+5 cells were expanded to 1.5E14 (i.e., 300,000,000-fold) which supports the conclusion that the CD133+ phenotype can be sustained (FIG. 3). If the initial culture period was 14 days before weekly reisolation began, there was a slight decrease in the total number and percentage of CD133+ cells (FIGS. 1, 2). An initial culture period of 21 days resulted in the near complete loss of sustained growth of CD133+ cells. In the absence of reisolation with regular feeding, CD133+ cells expanded initially but eventually died (no reisolation).

Conclusions

Freshly isolated CD133+ cells divide asymmetrically to produce daughter cells that are CD133+ and CD133−. We show here that with relatively short initial culture duration followed by subsequent removal of the CD133− cells, CD133+ cells maintain the ability to continue asymmetric division with production of CD133+ daughter cells. That is, if the CD133− cells are not removed weekly, the remaining CD133+ cells differentiate and lose the ability to generate CD133+ daughter cells. Freshly isolated CD133+ cells produce a large proportion (60-80%) of CD133+ daughters within the first week. With time in culture and weekly reisolation of the CD133+ cells (removal of CD133− cells), this percentage declined over about 3 weeks until reaching a plateau of sustained production of about 20-30% CD133+ daughter cells that can be maintained indefinitely in this sustained phenotype.

Example 2

Methods

CD133+ cells were separately isolated from cord blood buffy coats using immunomagnetic beads from three cord blood units. These three freshly isolated populations of cells were individually frozen at −80° C. A portion of the cells from each of these three fresh isolates were put into co-culture with adherent mesenchymal stem cells. Each week, CD133+ cells were reisolated to remove CD133− cells. After the fourth reisolation, CD133+ cells were frozen at −80° C. Cells from fresh isolates (n=3) and after four reisolations (n=3) were used for Trizol extraction of RNA. Two hundred nanograms (ng) of total RNA was then analyzed by next generation RNA sequencing with Science Exchange (available on the World Wide Web at scienceexchange.com), a contract research organization on the campus of the University of California, Los Angeles (see the World Wide Web at youtu.be/9gEONcrFDDk). Following quality control for RNA integrity for each sample, libraries were constructed, sequencing performed on a HiSeq3000 instrument, and data analysis performed.

Results

Expression of over 500 genes was significantly different ($p<0.05$) between freshly isolated CD133+ cells and CD133+ cells after four reisolations. Shown in Table 1 are transcription factors and growth factors that, compared to freshly isolated CD133+ cells, were differentially expressed in the CD133+ cells after four reisolations that are important in regulation of a primitive growth phenotype typically associated with embryonic stem cells and/or induced pluripotent stem cells (iPSCs).

TABLE 1

| Transcription Factors, Growth Factors | logFC | PValue | |
|---|---|---|---|
| FOXA2 | 9.03 | 9.1E−22 | |
| HOXA1 | 2.87 | 7.4E−09 | |
| MKI67 | 2.84 | 7.27E−60 | |
| PCNA | 2.03 | 4.81E−48 | |
| FLT3 | −0.39 | 1.8E−02 | |
| RUNX2 | −0.46 | 1.3E−03 | |
| TCF4 | −0.51 | 1.13E−04 | |
| POU5F1 | −1.07 | 1.5E−05 | |
| SOX4 | −1.18 | 3.0E−16 | |
| TCF7 | −2.36 | 3.2E−05 | |
| KLF1 | −2.45 | 4.1E−05 | |
| BMP3 | −3.43 | 1.9E−05 | |
| GATA1 | −5.02 | 6.9E−15 | |
| GATA3 | −7.81 | 1.3E−48 | |
| IL18R1 | −8.00 | 5.5E−31 | |
| GDF10 | −8.14 | 1.8E−15 | |
| NANOG | −0.21 | 6.08E−01 | n.s. | logFC, log fold change;
n.s., not significantly changed ($p > 0.05$).

Conclusions

Repeated isolation selects for a CD133+ cell population that, relative to the population of CD133+ cells freshly isolated from umbilical cord blood, overexpresses transcription factors and growth factors typically associated with a very primitive growth phenotype.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An isolated human CD133+ cell population expressing at least one mRNA selected from FOXA2, HOXA1, MKI67, and PCNA at a higher level than naturally occurring human CD133+ cells, at least one mRNA selected from TCF7, KLF1, BMP3, GATA1, GATA3, IL18R1, and GDF10 at a lower level than naturally occurring human CD133+ cells, or a combination thereof.

2. The isolated human CD133+ cell population of claim 1 wherein 1, 2, 3, or all 4 mRNAs selected from FOXA2, HOXA1, MKI67, and PCNA are expressed at a higher level in isolated CD133+ cells present in the population than in the naturally occurring human CD133+ cells.

3. The isolated human CD133+ cell population of claim 1 wherein 1, 2, 3, 4, 5, 6, or all 7 mRNAs selected from TCF7, KLF1, BMP3, GATA1, GATA3, IL18R1, and GDF10 are expressed at a lower level in isolated CD133+ cells present in the population than in the naturally occurring human CD133+ cells.

4. The isolated human CD133+ cell population of claim 1 wherein a combination of one or more mRNAs selected from FOXA2, HOXA1, MKI67, and PCNA are expressed in isolated CD133+ cells present in the population at a higher level than the naturally occurring human CD133+ cells and a combination of one or more mRNAs selected from TCF7, KLF1, BMP3, GATA1, GATA3, IL18R1, and GDF10 are expressed in isolated CD133+ cells present in the population at a lower level than the naturally occurring human CD133+ cells.

5. The isolated human CD133+ cell population of claim 1 wherein the difference in expression of the mRNA in the isolated CD133+ cells present in the population compared to the naturally occurring human CD133+ cells is statistically significant.

6. The isolated human CD133+ cell population of claim 1 wherein isolated CD133+ cells present in the population grow at a rate that is greater than the naturally occurring human CD133+ cells.

7. The isolated human CD133+ cell population of claim 1 wherein the naturally occurring human CD133+ cells are from cord blood.

8. An isolated human CD133+ cell from the isolated CD133+ cell population of claim 1.

9. A method for producing an expanded population of CD133+ cells, comprising:
  (a) providing a sample comprising isolated human CD133+ cells originating from a hematopoietic source;
  (b) incubating the CD133+ cells for at least 1 day in a first culture under conditions suitable for division of the CD133+ cells;
  (c) reisolating the CD133+ cells present in the first culture to result in reisolated CD133+ cells;
  (d) incubating the reisolated CD133+ cells for at least 1 day in a second culture under conditions suitable for division of the CD133+ cells, and reisolating the CD133+ cells present in the culture; and either
  (e) repeating the incubating and the reisolating of step (d) until the reisolated CD133+ cells are cultured at least 21 days after the reisolating of step (c) or
  (f) repeating the incubating and the reisolating of step (d) until at least 15% of the cells after the at least 1 day incubation in the second culture are CD133+.

10. The method of claim 9 further comprising isolating human CD133+ cells from human CD133− cells to result in the sample.

11. The method of claim 9 wherein the hematopoietic source comprises bone marrow, peripheral blood, blood vessel, lymph, umbilical cord blood, or Wharton's jelly.

12. The method of claim 9 wherein the sample comprises banked umbilical cord blood.

13. The method of claim 9 wherein the sample is fresh or frozen.

14. The method of claim 9 wherein the incubating of step (b) comprises incubating the CD133+ cells for at least 4 days in the first culture.

15. The method of claim 9 wherein the incubating of step (b) is for no greater than 21 days.

16. The method of claim 9 wherein the incubating of step (d) comprises incubating the reisolated CD133+ cells for at least 4 days in the second culture.

17. The method of claim 9 wherein the cells are modified.

18. The method of claim 9 wherein the cells are non-modified.

19. The method of claim 9 wherein the first and second culture conditions comprise a mesenchymal stem cell (MSC) feeder cell layer.

20. The method of claim 9 wherein the incubating of (b) is for no greater than 21 days and the incubating of (d) is for no greater than 21 days.

21. The method of claim 9 wherein the reisolated CD133+ cells of (e) or (f) are hematopoietic stem cells.

22. A method comprising:
  providing human CD133+ cells that have been cultured ex vivo for at least 21 days, wherein the CD133+ cells originated from a hematopoietic source;
  culturing the human CD133+ cells for at least 1 day and no greater than 20 days under conditions suitable for division of the CD133+ cells; and
  isolating the CD133+ cells present in the culture wherein at least 15% of the cells after the culturing are CD133+.

23. The method of claim 22 further comprising expanding the number of CD133+ cells by repeating the culturing and isolating steps at least once.

24. The method of claim 22 wherein the culturing comprises a mesenchymal stem cell (MSC) feeder cell layer.

* * * * *